United States Patent [19]

Rocco

[11] 4,233,983
[45] Nov. 18, 1980

[54] CATHETER PROVIDED WITH A SAFETY-FIXING MEMBER, REMOTELY ADJUSTABLE AND EXPANDIBLE BY INTRODUCING FLUIDS

[76] Inventor: Francesco Rocco, Via Fogazzaro, 20, 20100 Milano, Italy

[21] Appl. No.: 908,382

[22] Filed: May 22, 1978

[30] Foreign Application Priority Data

May 30, 1977 [IT] Italy ................... 21426 A/77
Oct. 26, 1977 [IT] Italy ................... 22581 A/77

[51] Int. Cl.³ ............................................. A61M 25/00
[52] U.S. Cl. ................................. 128/349 B; 128/246
[58] Field of Search ......... 128/246, 325, 344, 348–351

[56] References Cited

U.S. PATENT DOCUMENTS

| 2,173,527 | 9/1939 | Agayoff | 128/349 B |
| 2,849,001 | 8/1958 | Oddo | 128/349 B X |
| 3,044,468 | 7/1962 | Birtwell | 128/349 B |
| 3,154,078 | 10/1964 | Goodrich | 128/349 B X |
| 3,438,375 | 4/1969 | Ericson | 128/349 B |
| 3,954,110 | 5/1976 | Hutchison | 128/349 B |

Primary Examiner—Dalton L. Truluck
Attorney, Agent, or Firm—Bucknam and Archer

[57] ABSTRACT

A retention catheter in which a closed forward end portion of the drainage tube is provided with a pair of resilient inflatable bags which serve to retain the catheter end in an established drainage position. The bags extend circumferentially about the tube in diametrical opposition and along the same length portion of the tube, with the circumferential extent of each bag being so limited as to define on the tube wall a pair of opposed oblong open windows through which fluid drainage occurs. One duct extends along the tube wall to carry fluid for inflating the bags, and another duct communicates the bags with each other to equalize their inflation.

5 Claims, 9 Drawing Figures

U.S. Patent    Nov. 18, 1980    Sheet 1 of 3    4,233,983
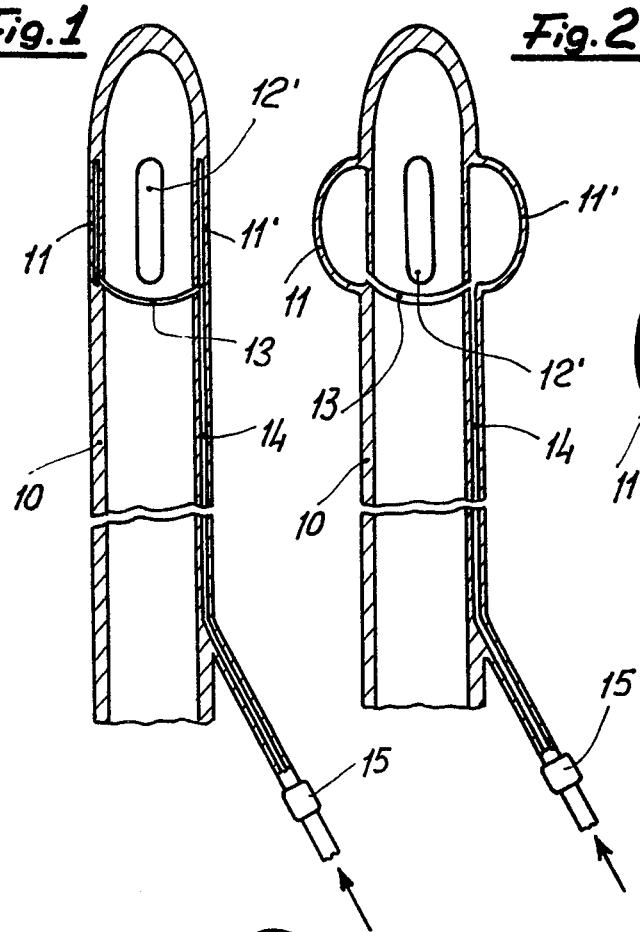

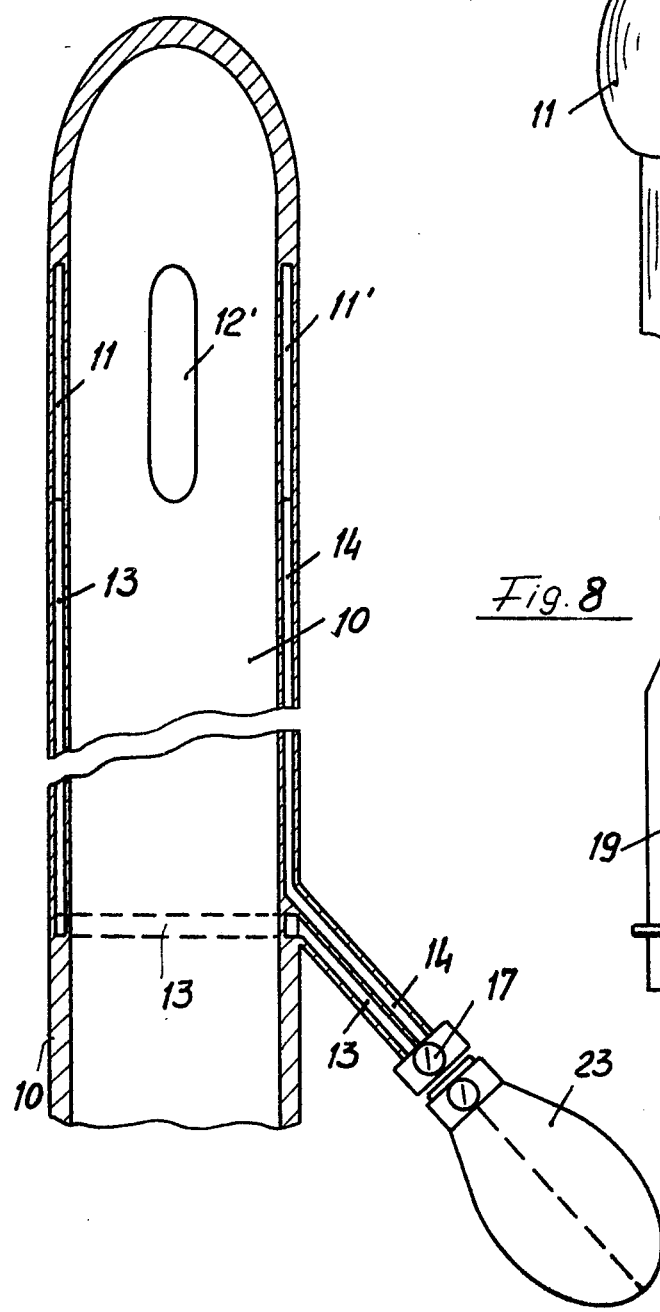
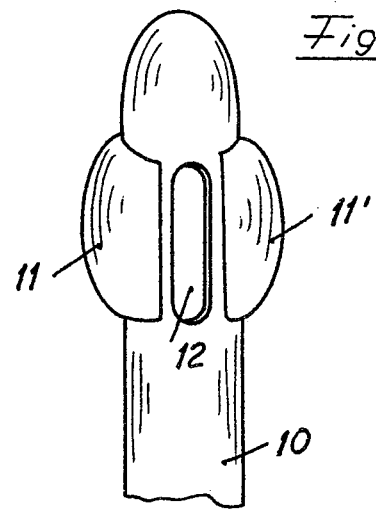
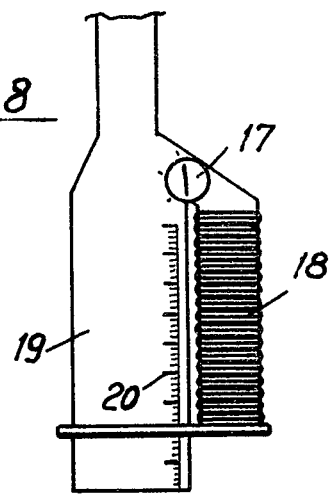

CATHETER PROVIDED WITH A SAFETY-FIXING MEMBER, REMOTELY ADJUSTABLE AND EXPANDIBLE BY INTRODUCING FLUIDS

BACKGROUND

This invention relates in general to catheters, and more particularly to a retention catheter as is commonly used in the practice of medicine, particularly in urology.

As is well known in the medical arts, a catheter used in urology typically has a flexible tube that is introduced through the urinary duct to reach the vesica, or in certain cases, the kidneys for the purpose of draining urine or other fluid therefrom.

Such catheters require means, typically in the form of inflatable members, that are effective to securely and firmly provide a safety-fixing of the catheter in an established drainage position throughout the period of its use. Without such safety-fixing provisions, there is a danger of the catheter tube dislocating from its intended drainage position, and unthreading through the insertion duct of the patient.

Until the present, several techniques have been developed in catheter construction to achieve retention of the catheter tube at the desired drainage location, but these various techniques have in one way or another presented certain problems.

Some of these problems arose in connection with catheters used with male patients wherein the urinary ducts are less accessible than female patients.

It has been found generally that the retention member or members provided for a catheter, in order to firmly fix the drainage position thereof, must be adjustable in size from a minimum size permitting the catheter to be introduced into the inlet duct of the organ to be drained, up to a retention configuration size that is necessarily larger than that of the inlet duct.

In the case of any catheter, whatever retention member or members are used, there has to be assured drainage at the most declining, or deepest point.

In some types of prior art catheters, a bulb type retention member was applied to the insertion end of the catheter, and such bulb did give some interference with draining the body cavity at the most declining portion thereof, because of an inappropriate location of the drainage hole in the catheter tube in relation to the retention bulb.

In certain other types of retention catheters, satisfactory drainage has been achieved, but in order to achieve such desired results, it was necessary to use complex means and procedures for adjusting the size of the retention member for a better location in situ of the catheter.

Catheters inserted into a patient eventually have to be removed, and in a case of certain prior art retention catheters, it was difficult to achieve a sufficient size reduction of the retention member as would allow unthreading of the catheter without damage to the urinary duct.

SUMMARY OF THE INVENTION

It is a main object of the invention to provide a retention catheter of a type aforesaid, which is of a construction that can be easily inserted, secured at a drainage location, and removed from the patient painlessly.

Another object of the invention is to provide a catheter as aforesaid that is capable of providing a reliable drainage at the most declining point of the organ into which it is introduced.

In general, the invention provides a catheter with a drainage tube having a closed forward end portion disposed for insertion into a body cavity to drain fluid therefrom, the wall of this tube circumferentially extending to define a lumen with a passage of the fluid to be drained, and a pair of resilient inflatable bags connected to the wall of the tube at the forward end portion thereof to serve as retention members. These bags extend circumferentially about the tube in diametrically opposed relation to each other and extend lengthwise along the tube over approximately the same length portion of the tube. The circumferential extension of each of the bags is limited so as to define on the tube wall a pair of spaces each between the bags and disposed in diametrically opposed relation to each other. For entry of fluid into the tube, there are provided a pair of opposed oblong open windows in the tube wall, each window being located in a respective one of the spaces between the bags, and each window extending lengthwise along the tube over approximately the same length portion as extend the bags. For inflation and deflation of these bags, there is provided a first duct communicating with the bags and extending lengthwise along the tube wall for carrying the fluid to inflate the bags, and a second duct communicating the bags with each other to equalize the inflation thereof.

As an additional feature, the catheter of the invention can be provided with a small pump prefilled with a precise amount of liquid to be injected into the bags for the inflation thereof.

In order to obtain an advantageous equal inflation of the bags, these can be individualy connected, through corresponding small tubes, to a small pump that is subdivided, by means of a septum, into two tanks containing respective predetermined amounts of liquid to be conveyed to the bags.

Alternatively, this same basic result can be achieved by means of a bellows pump that is coupled to the base of the drainage tube for support thereby, and which bellows body is constructed in such a manner as to be axially compressible parallel to the tube for injecting into the bags the fluid for inflating them. In such case, there can be included on the tube graduation marks indicating the degree of compression of the bellows body. At the top of such bellows pump, a valve can be located for controlling the outflow of the pump.

The flexibility of such pump should be less than that of the bags to be inflated, in order to prevent such bags from evacuating fluid when the pump valve is opened.

By controlling the inflation of the retention bags, it is thus possible to firmly fix the catheter in its operating position, and this adjustment can be made at a location external to the patient, which is where the pump or other means for controlling the amount of introduced inflation fluid is located.

The retention bags may of course be deflated as by opening a check valve at the control location so as to cause the inflation fluid to exit said bags thereby allowing the resiliency of the bag material to return to the original catheter tube insertion configuration as will allow a painless and damageless withdrawl of the catheter from the patient.

The various features and advantages of the invention will become apparent from the following detailed description and accompanying drawings related thereto.

BRIEF DESCRIPTION OF THE DRAWINGS

In the drawings:

FIG. 1 is an axial schematic sectional view of the operating portions of a catheter apparatus according to a preferred embodiment of the invention, in which catheter apparatus the retention bags are shown in an uninflated state.

FIG. 2 is a schematic axial section view similar to FIG. 1, but showing the catheter apparatus with the retention bags in an inflated state.

FIG. 3 is a transverse cross-section view of the catheter apparatus shown in FIG. 1, as taken through the retention bags thereof to show such bags in an uninflated state.

FIG. 4 is a transverse cross-sectional view taken similar to that of FIG. 3, but showing the retention bags in an inflated state, as shown axially in FIG. 2.

FIG. 5 is a perspective view of the forward end portion of the catheter apparatus shown in FIG. 2.

FIG. 6 is a schematic axial section view of a catheter apparatus similar to that shown in FIG. 1, but modified in accordance with another embodiment of the invention to utilize a special inflating pump arrangement.

FIG. 7 is a perspective view of the forward end portion of the catheter apparatus shown in FIG. 6 as seen with the retention bags shown in an inflated condition.

FIG. 8 is a longitudinal schematic view of the outside end portion of a catheter apparatus modified according to another embodiment of the invention and having a bellows pump for inflating the retention bags.

DESCRIPTION OF PREFERRED EMBODIMENT OF THE INVENTION

Figure 9:
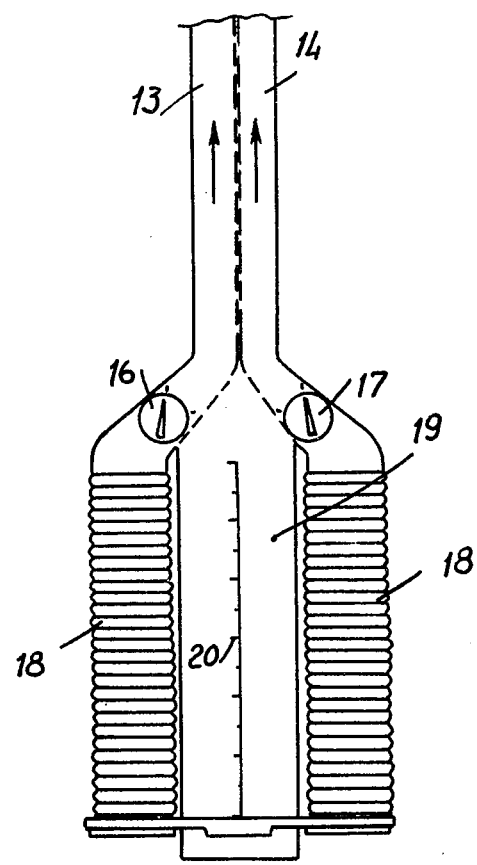
FIG. 9 is a longitudinal schematic view of the outside end portion of a catheter apparatus modified in accordance with a further embodiment of the invention and having two bellows pumps, each operable to control the inflation of a respective retention bag.

Referring to the drawing FIGS. 1-7, the catheter according to the present invention generally comprises a tube 10, of known type and made of a flexible material. At the forward end portion of tube 10, there is a closed tip, suitably shaped depending on the use, and two thin diametral opposed retention members in the form of bags 11 and 11'. These bags 11, 11' being resilient and inflatable to the configuration shown in FIGS. 2, 4, 5 and 7.

Between bags 11, 11' two similar oblong windows 12 and 12' are provided in tube 10, said windows 12, 12' being located diametrically opposite but with the centerlines thereof radially located at 90° with respect to the centerlines of the bags 11, 11' on tube 10, and the length of said windows, 12, 12' measured axially of the tube 10, being approximatively equal to the length of said pockets 11, 11'.

In particular, the lower or forward ends of windows 12 and 12' should be at a level equal to the forward or lower level of the bags 11, 11'.

Bags 11, 11' are connected to each other by a narrow duct 13 which, in turn, connects said bags 11, 11' to another duct 14 running lengthwise of the tube 10, back toward the outside end portion thereof where a check valve 15 is installed. Alternatively, each bag 11, 11' can be provided with an individual duct 13, 14 for inflation purposes as shown in FIG. 6.

The catheter of FIGS. 1-5 operates in the following manner: upon locating the forward end portion thereof, in which said windows 12, 12' are formed, in the duct 14 a fluid, preferably water, is introduced through one o more valves 15 thereby causing said bags 11 and 11' to inflate by an amount corresponding to the quantity of water introduced.

Thus the bags 11, 11' each is an adjustable fixing member, since they locate at the resting line of the vesica, in the kidney or at any suitable position.

Due to the fact that the corresponing windows 12 and 12' are at the same level, a complete outflow or the urine is obtained, the urine draining through the lumen of tube 10.

To withdraw the catheter, the valve 15 is opened, thereby draining the inflating fluid from the bags 11 and 11' which become flaccid and deflate, thereby returning to their uninflated configuration which allows the catheter to be unthreaded quickly and without damaging the inner walls of the urinary duct.

The catheter can, if desired, be also provided with a plurality of windows 12, 12' and bags 11, 11', more than a pair of each and related inflation/deflation ducts can be also separate and each provided with a valve (not shown).

As exemplified in FIGS. 8 and 9, the catheter can be provided with a bellows pump 18, suitably coupled to the base portion 19 of the tube 10, so that the pump 18 may be axially compressed while remaining generally parallel to the tube 10 itself. In this embodiment, on tube portion 19 suitable graduations 20 are provided and at the top of the pump 18 is optionally located a valve 17 operable to direct the fluid to either the aforesaid ducts 13 and 14.

In FIG. 9, two bellows pumps 18 are provided, each bellows pump 18 being connected to a respective duct 13, 14 through a corresponding valve 16, 17.

In particular, the fluid for inflating bags 11, 11' may be either an x-ray opaque liquid or water.

It should moreover be pointed out that the bags 11 and 11' are of such thickness and resiliency as to cause the inflation liquid to be reconveyed to the bellows pumps 18 as the valve or valves 16 and 17 are opened in preparation for extracting the catheter from the patient. It is also to be noted that the provision of the catheter with pumps 18, 23 is an option since the bags 11, 11' of the catheter can be inflated with liquid by using a syringe according to a conventional practice.

As can be seen from FIG. 6, the pump 23 is in effect a squeeze bulb that is subdivided, by means of a septum into two tanks containing respective predetermined amounts of liquid to be conveyed into the bags 11, 11' respective ducts 13, 14.

I claim:

1. A catheter apparatus which comprises a tuve having a closed forward end portion disposed for insertion into a body cavity to drain fluid therefrom, the wall of said tube circumferentially extending to define a lumen for passage of said fluid; a pair of resilient inflatable bags connected to the wall of said tube at the forward end portion thereof, said bags extending circumferentially about said tube in diametrically opposed relation to each other and extending lengthwise along the tube over approximately the same length portion of the tube, said bags being limited in circumferential extension to define on the tube wall a pair of spaces each between said bags and disposed in diametrically opposed relation to each other; means defining a pair of opposed oblong open windows in said tube wall, each window being located in a respective one of said spaces and extending lengthwise along the tube over approximately the same length portion as extend said bags; a first duct communicating with said bags and extending lengthwise along the tube wall for carrying a fluid to inflate said bags, and a second duct extending circumferentially within said tube wall communicating said bags with each other to equalize the inflation thereof.

2. A catheter apparatus which comprises a tube having a closed forward end portion disposed for insertion into a body cavity to drain fluid therefrom, the wall of said tube circumferentially extending to define a lumen for passage of said fluid; a pair of resilient inflatable bags connected to the wall of said tube at the forward end portion thereof, said bags extending circumferentially about said tube in diametrically opposed relation to each other and extending lengthwise along the tube over approximately the same length portion of the tube, said bags being limited in circumferential extension to define on the tube wall a pair of spaces each between said bags and disposed in diametrically opposed relation to each other; means defining a pair of opposed oblong open windows in said tube wall, each window being located in a respective one of said spaces and extending lengthwise along the tube over approximately the same length portion as extend said bags; a first duct communicating with said bags and extending lengthwise along the tube wall for carrying a fluid to inflate said bags, and a second duct communicating said bags with each other to equilize the inflation thereof; and including a pump flow connected by a fixing ring to said first duct, said pump including a reservoir subdivided by an intermediate septum into two compartments each of a size to contain a respective predetermined amount of liquid for delivery through said first duct to inflate said bags.

3. A catheter apparatus which comprises a tube having a closed forward end portion disposed for insertion into a body cavity to drain fluid therefrom, the wall of said tube circumferentially extending to define a lumen for passage of said fluid; a pair of resilient inflatable bags connected to the wall of said tube at the forward end portion thereof, said bags extending circumferentially about said tube in diametrically opposed relation to each other and extending lengthwise along the tube over approximately the same length portion of the tube, said bags being limited in circumferential extension to define on the tube wall a pair of spaces each between said bags and disposed in diametrically opposed relation to each other; means defining a pair of opposed oblong open windows in said tube wall, each window being located in a respective one of said spaces and extending lengthwise along the tube over approximately the same length portion as extend said bags; a first duct communicating with said bags and extending lengthwise along the tube wall for carrying a fluid to inflate said bags, and a second duct communicating said bags with each other to equalize the inflation thereof; and including a pump comprising a bellows body coupled to the base of said tube in such a manner as to be axially compressible parallel to said tube, said bellows body being disposed to contain liquid for delivery through said ducts to inflate said bags upon compression of said bellows body, said tube having graduations indicating the degree of compression of the bellows body and hence the amount of liquid delivered to inflate said bags, and a valve at said pump to control the outflow of liquid therefrom.

4. A catheter apparatus according to claim 3 characterized in that said bags are of such thickness and resiliency as to cause the inflation liquid to automatically return through said first and second ducts as the catheter is withdrawn from the body cavity.

5. A catheter apparatus according to claim 3 characterized in that there are included two of said bellows bodies each connected to a respective one of said first and second ducts by a respective valve.

* * * * *